(12) United States Patent
Wen et al.

(10) Patent No.: US 8,202,713 B2
(45) Date of Patent: Jun. 19, 2012

(54) PRODUCING EICOSAPENTAENOIC ACID (EPA) FROM BIODIESEL-DERIVED CRUDE GLYCEROL

(76) Inventors: Zhiyou Wen, Blacksburg, VA (US); Sncha Athalye, Raleigh, NC (US)

( * ) Notice: Subject to any disclaimer, the term of this patent is extended or adjusted under 35 U.S.C. 154(b) by 405 days.

(21) Appl. No.: 12/466,653

(22) Filed: May 15, 2009

(65) Prior Publication Data
US 2009/0286292 A1    Nov. 19, 2009

Related U.S. Application Data

(60) Provisional application No. 61/128,128, filed on May 19, 2008.

(51) Int. Cl.
*C12P 7/64*    (2006.01)

(52) U.S. Cl. ........................................ 435/134; 435/171
(58) Field of Classification Search ........................ None
See application file for complete search history.

(56) References Cited

OTHER PUBLICATIONS

Cheng et al., Bioresource Technology, 1999, vol. 67, p. 101-110.*
Chen et al., The Journal of Microbiology, 2003, vol. 41, No. 3, p. 252-258.*
Pyle et al., J Agric. Food Chem., May 2008, vol. 56, p. 3933-3939.*

* cited by examiner

*Primary Examiner* — Kade Ariani
(74) *Attorney, Agent, or Firm* — McDonald Hopkins LLC

(57) ABSTRACT

*Pythium*, when cultured with crude glycerol as a carbon source, produces useful polyunsaturated fatty acids such as eicosapentaenoic acid (EPA). The crude glycerol is pretreated to remove soaps and methanol. An exemplary *Pythium* species for use in the production of EPA is *Pythium irregulare*.

14 Claims, 4 Drawing Sheets

PRODUCING EICOSAPENTAENOIC ACID (EPA) FROM BIODIESEL-DERIVED CRUDE GLYCEROL

CROSS-REFERENCE TO RELATED APPLICATIONS

This application claims benefit of U.S. provisional patent application 61/128,128, filed May 19, 2008, the complete contents of which is hereby incorporated by reference.

DESCRIPTION

Background of the Invention

1. Field of the Invention

The invention generally relates to the production of fatty acids such as eicosapentaenoic acid (EPA) from crude glycerol. In particular, the invention provides methods and compositions for the preparation of fatty acids such as EPA from crude glycerol using the fungus (oomycete) *Pythium*.

2. Background of the Invention

Eicosapentaenoic acid (EPA, C20:5, n-3) is an important fatty acid in the omega-3 family based on its medically established therapeutic capabilities against cardiovascular diseases, cancers, schizophrenia, and Alzheimer's disease (Simopoulos, A. P. Essential fatty acids in health and chronic disease. Am. J. Clin. Nutr. 1999, 70, 560S-569S; Ursin, V. M. Modification of plant lipids for human health: development of functional land-based omega-3 fatty acids. J. Nutr. 2003, 133, 4271-4274). However, a microbial-based EPA source has not been commercially available. Fish oil as the main source of EPA has several limitations such as undesirable taste and odor, heavy metal contamination, and potential shortage due to overfishing, variation in seasonal availability of source fish, and cost of production. Thus, it would be highly beneficial to identify and develop new sources to produce EPA.

Biodiesel as an alternative fuel has attracted increasing attention in recent years. In the United States, for example, the annual biodiesel production has increased sharply from <100 million gallons prior to 2005 to 700 million gallons in 2008. During the biodiesel production process, crude glycerol is created as a byproduct. In general, for every gallon of biodiesel produced, 0.3 kg of glycerol is produced. With biodiesel production growing exponentially, the market is being flooded with crude glycerol. Some uses for this crude product have been developed (e.g. combustion, composting, anaerobic digestion, or feeding for various animals such as pigs and chickens). Converting crude glycerol into value-added products through thermochemical or biological methods is another alternative for utilizing this waste stream. However, the amount of crude glycerol being produced still far exceeds the demand for these uses. Because it is prohibitively expensive to convert and purify the crude glycerol into material that can be used for food, cosmetics, or pharmaceutical industries, biodiesel producers are actively searching for new uses for crude glycerol. There is therefor an ongoing need to discover and develop new methods of using crude glycerol in a constructive manner.

SUMMARY OF THE INVENTION

The present invention solves the problem of the accumulation of excess crude glycerol while, at the same time, providing a cost-effective means to produce valuable fatty acids such as eicosapentaenoic acid (EPA). The invention is based on the discovery that the fungus, *Pythium* irregulare, produces EPA from crude glycerol. It had been reported that *P. irregulare* is capable of utilizing a variety of other organic waste streams for producing EPA (Cheng, M. H.; Walker, T. H.; Hulbert, G. J.; Raman, D. R. Bioresour. Technol. 1999, 67, 101-110). However, prior to the present invention, it was not known that the fungus could produce EPA from crude waste glycerol.

It is an object of this invention to develop an optimized process for growing a fungus (oomycete) such as *P. irregulare* on biodiesel-derived crude glycerol and produce high levels of EPA. Thus, the invention provides a method of producing a fatty acid-rich biomass from crude waste glycerol. The method comprises the steps of 1) providing crude glycerol culture medium that is substantially free of soaps and methanol; and 2) culturing *Pythium* in said crude glycerol culture medium under conditions that permit said *Pythium* to use glycerol in said crude glycerol culture medium as a carbon source to produce a fatty acid-rich biomass. In one embodiment, the *Pythium* is *Pythium* irregulare. In some embodiments, the fatty acid-rich biomass comprises eicosapentaenoic acid (EPA). In addition, the said step of providing may include a step of removing soaps and methanol from the crude waste glycerol. In some embodiments of the invention, the crude glycerol culture medium further comprises one or more oils, e.g. flaxseed oil and/or soybean oil. In some embodiments, the crude glycerol is present in the crude glycerol culture medium at a concentration of 30 grams per liter. In other embodiments, the crude glycerol culture medium further comprises 10 g/L of yeast extract.

The invention also provides a method of producing eicosapentaenoic acid (EPA) from crude waste glycerol. The method comprises the steps of 1) providing crude glycerol culture medium; and 2) culturing *Pythium* in the crude glycerol culture medium under conditions that permit the *Pythium* to use glycerol in the crude glycerol culture medium as a carbon source to produce biomass that includes EPA. In one embodiment of the invention, the *Pythium* is *Pythium* irregulare. In another embodiment, the step of pretreating includes removing soaps and methanol from the crude glycerol. In yet other embodiments, the crude glycerol culture medium further comprises one or more oils, for example, flaxseed oil and/or soybean oil. In some embodiments, the crude glycerol is present in the crude glycerol culture medium at a concentration of 30 grams per liter. In other embodiments, the crude glycerol culture medium further comprises 10 g/L of yeast extract.

The invention further provides *Pythium* biomass that comprises eicosapentaenoic acid (EPA). According to the invention, at least a portion of the biomass and at least a portion of the EPA is produced by *Pythium* using crude glycerol as a substrate.

DETAILED DESCRIPTION

Figure 1A:
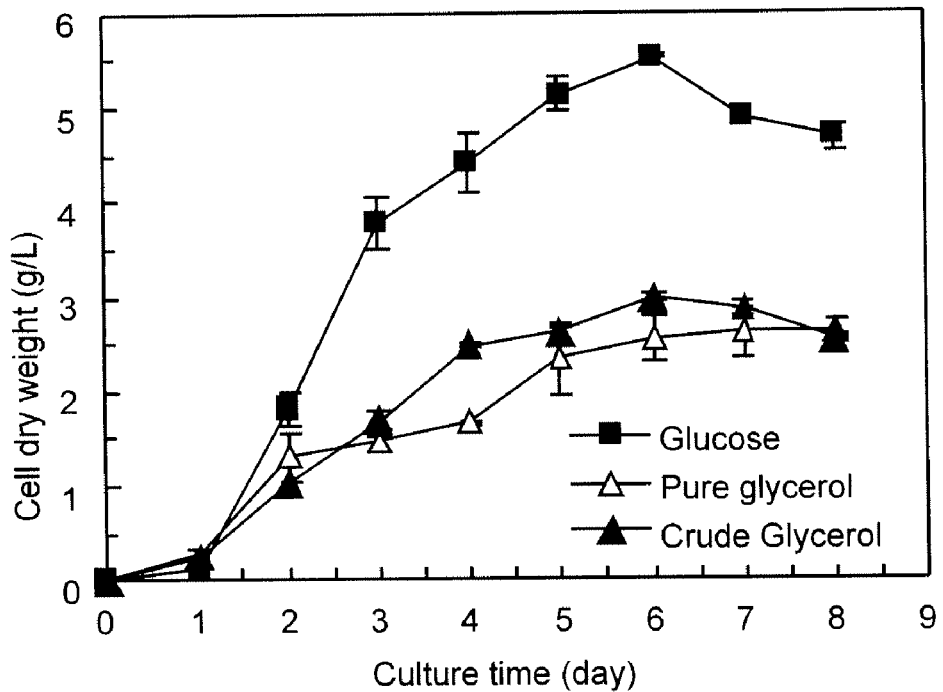
FIGS. 1A and B. Time course of cell growth (A) and substrate consumption (B) of *P. irregulare* with glucose, pure glycerol, and crude glycerol as substrate.

The invention provides a cost-effective means to produce useful fatty acids such as the omega-3 polyunsaturated fatty acid eicosapentaenoic acid (EPA) while, at the same time, addressing the problem of the accumulation of excess crude glycerol. The invention is based on the discovery that the fungus *Pythium* produces EPA from crude glycerol, in particular from crude glycerol from which soaps and methanol have been removed. According to the invention, *Pythium* is cultured with waste glycerol under conditions that allow the microorganism to use the waste glycerol as a substrate for the production of various fatty acids of interest, e.g. EPA. The resulting biomass is rich in fatty acids, including EPA and, after suitable processing (e.g. drying), may be used as a food source or food additive. Alternatively, one or more fatty acids of interest may be isolated from the biomass prior to use.

Those of skill in the art will recognize that *Pythium* organisms were previously classified as fungi but are now known to have evolved separately from fungi, and to be more closely related to brown algae and diatoms. Their current classification is: Kingdom: Chromalveolata; Phylum: Heterokontophyta; Class: Oomycetes; Order: Pythiales; Family: Pythiaceae; Genus: *Pythium*. *Pythium* represent a group of filamentous, unicellular organisms which physically resemble fungi, and are often treated or referred to as such due to their previous classification. Herein, these organisms may be referred to either as fungi, or according to the newer classification, e.g. as oomycetes. Exemplary species of *Pythium* that may be used in the practice of the invention include but are not limited to *P. irregulare*, *Pythium ultimum*, *Pythium insidiuosum*, *Pythium debaryanum*, *Pythium intermedium*, *Pythium megalacanthum*, *Pythium paroecandrum*, and *Pythium sylvaticum*.

The crude waste glycerol that is used to prepare the culture medium in which the *Pythium* is cultured may be obtained from any source, one example of which is biodiesel production. Biodiesel is made through a catalyzed transesterification between oils or fats (triglycerides) and an alcohol (usually methanol). Common feedstocks are pure vegetable oil (e.g., soybean, canola, sunflower), rendered animal fats, or waste vegetable oils. The theoretical ratio of methanol to triglyceride is 3:1; which corresponds to having one methanol molecule for each of the three hydrocarbon chains present in the triglyceride molecule, and is equivalent to approximately 12% methanol by volume. In practice, this ratio needs to be higher in order to drive the reaction towards a maximum biodiesel yield; 25% methanol by volume is recommended. The catalyst can be alkalis, acids, or enzymes (e.g., lipase). The majority of biodiesel produced today is made using an alkali (such as NaOH or KOH) catalyzed reaction because this reaction (1) requires only low temperature and pressure, (2) has a high conversion yield (98%) with minimal side reactions and a short reaction time, (3) is a direct conversion to biodiesel with no intermediate compounds, and (4) does not require specific construction materials. The glycerol backbone of the triglyceride remains as a waste product after the reaction is completed.

Crude glycerol generated from biodiesel production is impure and of little economic value. In general, glycerol makes up 65% to 85% (w/w) of the crude stream. The wide range of the purity values can be attributed to different glycerol purification methods or different feedstocks used by biodiesel producers. For example, Thompson and He (2006. Applied Engineering in Agriculture, 22, 261-265.) have characterized the glycerol produced from various biodiesel feedstocks. The authors found that mustard seed generated a lower level (62%) of glycerol, while soy oil had 67.8% glycerol, and waste vegetable oil had the highest level (76.6%) of glycerol. Any of these preparations may be used to make the crude glycerol culture medium that is utilized in the practice of the invention.

Methanol and free fatty acids (soaps) are the two major impurities contained in crude glycerol. The existence of methanol is due to the fact that biodiesel producers often use excess methanol to drive the chemical transesterification and do not recover all the methanol. The soaps, which are soluble in the glycerol layer, originate from a reaction between the free fatty acids present in the initial feedstock and the catalyst (base) as follows:

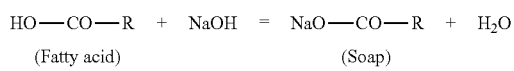

In addition to methanol and soaps, crude glycerol also contains a variety of elements such as calcium, magnesium, phosphorous, or sulfur, as well as potassium and sodium. Cadmium, mercury, and arsenic are generally below detectable limits.

As shown in the Examples below, the presence of soaps in the glycerol feedstock tend to inhibit the growth of *Pythium* and the production of fatty acids by the microorganism. Therefore, in some embodiments of the invention, soaps are at least partially removed from the crude glycerol prior to culturing the microorganism. Those of skill in the art will recognize that several methods for removing soaps from a liquid are known, and any suitable method may be utilized, so long as the resulting low-soap or substantially soap-free (i.e. less than about 1% residual soap) glycerol feedstock is capable of supporting the growth of *Pythium*, i.e. so long as other substances or conditions that may be harmful to *Pythium* culture are not retained in the low- or no-soap feedstock. For example, the crude glycerol derived from alkali-catalyzed transesterification usually has a dark brown color with a high pH (11-12). When used in microbial fermentations, crude glycerol is dissolved in a medium solution and the pH is usually adjusted to a neutral range. Under this condition, soaps will be converted into free fatty acids, as shown in the following equation

After pH adjustment, the free fatty acids in the crude glycerol stream result in a cloudy solution. After centrifugation, this cloudy solution separates into two clear phases, with the top layer being the free fatty acid phase, and bottom layer the glycerol phase. Thus, soaps may be precipitated from a crude glycerol solution by the addition of, for example, artificial seawater (pH 7.5) (See Kester, D. R., Duedall, I. W., Connors, D. N. and Pytkowicz, R. M. (1967). Limnology & Oceanography 12, 176-179; and Goldman, J. C. and McCarthy, J. J. (1978). Limnology & Oceanography 23, 695-703); or by the adjustment of the pH to a value that results in conversion of the soaps to fatty acids (e.g. to a pH of at least about 7.5, or further to pH 4 to 4.5 for a complete precipitation of free fatty acids). Once soaps are created, they may be separated and removed from the crude glycerol by any of several suitable means such as by centrifugation and separation of the resulting phases, settling, filtering, straining, etc. In some embodiments, the soaps are collected and reused in other processes.

The presence of methanol in the crude glycerol employed in the invention can also inhibit the growth of Pythium and thus methanol may also be removed by any suitable method. For example, due to its relatively high volatility, heating the crude glycerol (e.g. to a temperature of about 100° C. or greater). In some instances, this can be accomplished during sterilization of the crude glycerol, e.g. by autoclaving. In some embodiments, the methanol is evaporated and recaptured for reuse in another process.

Growth conditions for Pythium in the crude glycerol culture medium were studied as described in the Examples below. Generally, the crude waste glycerol is pretreated prior to culturing by removal of soaps and methanol, as these substances inhibit the growth of Pythium. The removal of soaps and methanol produces substantially soap- and substantially methanol-free crude glycerol, i.e. crude glycerol with less than about 1% residual soap or methanol. Herein, the initial glycerol waste (e.g. the waste that is a byproduct of biodiesel production) may be referred to as "crude glycerol" or "crude waste glycerol", whereas after removal of soaps and methanol, the solution may be referred to as "pre-treated crude glycerol" or "crude glycerol that is substantially free of soap(s) and methanol". After further preparation (e.g. dilution, supplementation, etc. as described below), a "crude glycerol culture medium" that is used to culture Pythium is produced.

Due to its high glycerol content, crude waste glycerol is a highly viscous liquid and is generally diluted even prior to soap and methanol removal by the addition of an aqueous diluent such as distilled water or artificial sea water. Dilution results in a solution of lower viscosity that is more readily manipulated (i.e. mixed, poured, etc.), and may, depending on the diluent that is used, also lower the pH and cause precipitation of soaps. The decrease in viscosity is important not only for pretreatment but also later during culturing, when the fungal culture must be aerated, sampled, transferred, etc. and high viscosity is detrimental to these processes. The extent of dilution will vary depending on the initial viscosity and glycerol concentration in the crude waste glycerol, which may vary from source to source. Further, dilution may also take into account the optimal amount of glycerol that is to be made available to the Pythium as a substrate in the finally formulated crude glycerol culture medium. Generally, the crude waste glycerol content of the crude glycerol culture medium is from about 10 to about 60 g/L of crude glycerol, or from about 20 to about 50 g/L of crude glycerol, and usually from about 30 to about 40 g/L of crude glycerol. A crude glycerol culture medium with a crude glycerol final concentration (before culturing begins) of from about 30 to about 40 g/L of glycerol generally has the desired properties of 1) being of a suitable viscosity; and 2) being of a sufficiently high concentration to support a Pythium culture to generate desired quantities of fatty acids. 30 g/L of crude glycerol (prior to removal of soaps and methanol) corresponds to an actual "glycerol" content of about 22 g/L (i.e. about 70% to 80% of crude glycerol is glycerol), since soaps, methanol and other impurities make up about 20-30% of the initial weight of the crude glycerol. Those of skill in the art will recognize that the actual amount of glycerol in a crude glycerol waste stream may vary from source to source. However, the fungi can readily adapt to such relatively minor fluctuations in final glycerol content in the crude glycerol culture medium, e.g. from about 20 to about 25 g/L.

In addition, other substances essential to the fungi growth need to be added to the crude glycerol culture medium. For example, yeast extract may be added to the culture medium in an amount generally ranging from about 1 to about 25 g/L, and usually from about 5 to about 10, 15 or 20 g/L. In most embodiments, the amount of yeast extract in the crude glycerol culture medium will be of a final concentration (i.e. prior to inoculation with Pythium) in the range of from about 5 to about 10 g/L, which is favorable for maximizing the production of the fatty acid EPA.

Thus, a basic crude glycerol culture medium for use in culturing Pythium in order to produce fatty acids such as EPA generally includes at least crude glycerol (usually pretreated) at a final concentration of from about 30 to 40 (e.g. about 30) g/L, and about 5 to 10 (e.g. about 10) g/L of yeast extract. The final crude glycerol culture medium generally has a pH in the range of from about 6.0 to about 6.5, is sterile, and has a viscosity that is suitable for culturing and later harvesting Pythium biomass.

Various other substances may be advantageously added to the crude glycerol culture medium. Examples of such substances include but are not limited to various salts, buffering agents, trace elements, vitamins, amino acids, etc. However, as described in the Examples section, one advantage of Pythium culture is that this organism is relatively hardy and does not require additional supplements in order to grow and produce fatty acid-enriched biomass. In some embodiments of the invention however, various oils are added to the crude glycerol culture medium, as these can enhance biomass and thus the overall production level of particular fatty acids such as EPA. This enhancement is due to oil absorption by the fungal cells and elongation of shorter chain fatty acids (e.g., linoleic acid and R-linolenic acid) into longer chain fatty acids (e.g., linoleic acid and alpha-linolenic acid) into longer chain fatty acids (e.g. EPA). Examples of suitable oils include but are not limited to soybean oil, flaxseed oil, canola oil, linseed oil, and corn oil. Generally, the amount of oil that is added is in the range of from about 0.5% to about 4% and usually is about 1%.

The preparation of fatty-acid enriched Pythium biomass on a commercial scale may be carried out using any suitable industrial equipment, e.g. tanks or reaction vessels capable of containing volumes of about 10 to 100 $m^3$. Such vessels are generally known to those of skill in the art, and may also comprise, in addition to a means of adding and removing medium, means for, for example, sampling the medium (e.g. to measure pH), means to monitor and adjust the temperature; means to supply gases (e.g. air, oxygen, etc.) to the culture; means to agitate the medium, etc.

In order to begin an industrial scale culture, a substantially pure Pythium culture is obtained (e.g. from the American Type Culture Collection or another suitable source) and used to initiate growth of Pythium under conditions favorable to spore formation e.g. growth for several (e.g. 3-7) days on agar slants supplemented with glucose and yeast extract, pH about 5.5 to about 6.0. To start the serial scale-up liquid cultures, an inoculum of Pythium spores is first prepared e.g. by washing the agar surface with distilled water, medium, etc. and the spore solution is added to a bench scale container suitable for large scale growth of the organism. The Pythium inoculum contains from about $10^5$ to about $10^7$ spores per liter of culture medium that is inoculated. Then, the culture is "stepped up" gradually by initially inoculating a small volume (e.g. 1-2 liters) which is subsequently transferred to a larger volume.

During culturing of the *Pythium*, the medium is agitated and air or oxygen (usually air) is supplied to the growing culture. Agitation may be performed, for example, by shaking or rotating the culture (e.g. at an rpm of about 150 tp 200 rpm, usually about 170 rpm) in a bench scale flask culture or by a means of agitation or stirring such as paddles, propellers, or another suitable mechanism in fermentor culture. In fermentor culture, the fermentor is aerated or oxygenated, usually oxygenated during growth. Generally, the oxygen concentration is maintained at a level of about 10% to about 50% throughout culturing. Those of skill in the art will recognize that the provision of air or oxygen to the culture may also serve to agitate the culture as the gas is blown into or bubbled through the medium.

Typically, in order to maximize the production of fatty acid-enriched biomass, the culturing of *Pythium* is carried out in two stages. After inoculation of culture medium with the microorganism, a growth phase is undertaken at a temperature of about 25-30° C. in order to encourage the accumulation of biomass. Generally, the culture is maintained at this temperature for a period of from about 4 to about 6 days, and usually for about 5 days. Thereafter, in order to promote the accumulation of fatty acids in the *Pythium* cells, the temperature is decreased to about 20° C. Culturing continues at this lower temperature for a period of from about 1 to about 3 days, and usually for about 2 days. Thus, the total number of days from initial inoculation to harvesting of the *Pythium* biomass is typically from about 5 to about 7 days, and usually is about 6 days.

Thereafter, the *Pythium* biomass is harvested by any of several suitable means and methods that are known to those of skill in the art, for example, by centrifugation and/or filtration. Subsequent processing of the biomass is carried out according to its intended use, e.g. by dewatering and drying.

*Pythium* cultured in a crude glycerol culture medium as described herein produces a biomass that is rich is a variety of fatty acids and may be used in a variety of applications. In some embodiments of the invention, the fatty acid enriched biomass that is produced by *Pythium* according to the methods of the invention is used "as is" i.e. the fatty acids are not separated or isolated from the biomass prior to use. In such embodiments, the biomass may be collected and used directly (e.g. as a wet fungal mass) but will more often first be treated by removing some or most or all of the water associated with the biomass. Thus, the invention also encompasses various forms of fully or partially dessicated (dried) biomass produced by *Pythium* that is enriched for fatty acids (e.g. EPA) due to having been cultured in the presence of crude glycerol as described herein. Such biomass may be used, e.g. as a food source or additive to feed a variety of organisms, e.g. fish (especially fish grown in aquacultural fish "farms"); chickens and other poultry (turkeys, Guinea hens, etc.); cows, sheep, goats, horses, and other domestic animals that are typically raised in a "farm" environment, etc. The biomass may be used as food for or to supplement the diet of any species that in any way benefits from the intake of fatty acids, especially EPA, to their diet. Of special interest may be the feeding of the biomass to laying hens to increase the quality (type) of the fatty acids in eggs, or to increase the amount of desired fatty acids in eggs. Similarly, the biomass may be fed to animals raised as food in order to increase the quality (type) of the fatty acids in meat, or to increase the amount of desired fatty acids in meat. Generally, such desired fatty acids include polyunsaturated fatty acids (PUFAs), and in particular, omega-3 fatty acids such as EPA.

In other embodiments of the invention, the fatty acids, especially EPA, may be separated from the biomass, i.e. substantially purified to varying degrees, and then used, e.g. as food supplements. Such fatty acids preparations may contain a mixture of one or more fatty acids originating from the *Pythium* biomass of the invention, or alternatively, the fatty acids may be isolated to provide one or more substantially pure fatty acids.

The biomass and/or fatty acids prepared according to the methods of the invention may be used for purposes other than for food. For example, various skin preparations, cosmetics, soaps, skin cleansers, lotions, sun screen, hair products and other preparations made be formulated to include either the biomass itself, or one or more fatty acids obtained from the biomass. In particular, various "natural" or "green" products may be prepared and marketed as containing biomass that is "naturally" enriched in valuable fatty acids, and which is ecologically responsible due to its preparation using waste crude glycerol.

EXAMPLES

Example 1

Producing EPA from Fungi Grown on Crude Glycerol

Some fungal species such as *Mortierella* and *Pythium* are capable of producing high levels of EPA. Compared to algal cultures, fungal cells are more resistant to negative growing environments and require simpler medium nutrients. In addition, fungal culture avoids light limitation, which often happens in algal photoautrophic or mixotrophic cultures. It has been reported that *Pythium irregulare* can grow and produce EPA on various substrates such as crude soybean oil, sucrose waste stream, and soybean waste stream (Cheng, M. H., Walker, T. H., Hulbert, G. J. & Raman, D. R. 1999. Bioresource Technology, 67, 101-110.). The wide adaptability of this species leads us to investigate the potential of using crude glycerol for EPA production by *P. irregulare*.

Experimental Protocols

Fungal Strain and Culture Conditions

*Pythium irregulare* (ATCC 10951) was grown on an agar slant (with 20 g/L glucose and 10 g/L yeast extract) at 25° C. for 7 days. The spores on the slant were suspended with sterilized water and maintained at 4° C. for later use. To investigate EPA production from crude glycerol, the spore solution was inoculated into medium containing different concentrations of crude glycerol and yeast extract. The medium was adjusted to pH 6.0 before being autoclaved at 121° C. for 15 min. The cells were grown in 250-mL Erlenmeyer flasks, each containing 50 mL of medium, incubated at 25° C. in an orbital shaker set to 170 rpm.

Crude Glycerol Characterization and Pretreatment

Crude glycerol was obtained from Virginia Biodiesel Refinery (West Point, Va.). The refinery used alkali-catalyzed transesterification to produce biodiesel from soybean oil. The crude glycerol had a high pH level (11-12) with dark brown color. Because the producer used excess methanol to drive the transesterification towards a maximum biodiesel yield, the crude glycerol contained methanol as a major residue which accounted for ~12.8% (w/w) of the crude glycerol stream.

Soap was also found in the crude glycerol stream due to side-reactions. The soaps can be split into free fatty acids and salt by adding a strong acid.

Considering the difficulty in determining the exact amount of soap dissolved in the crude glycerol solution, we used free fatty acid precipitated from the crude glycerol (Equation 1) as an estimation of the soap residue. It was found that soap accounted for 25.2% (w/w) of the crude glycerol stream.

When the crude glycerol was mixed with artificial seawater (pH 7.5), some soap also precipitated from the solution. Depending on the experimental conditions, the soap either remained in or was removed from the medium. To prepare soap-free medium, the following procedures were used: (i) the glycerol was mixed with distilled water at a ratio of 1:4 (v/v) to reduce the viscosity of the fluid, (ii) the pH of the fluid was adjusted to 3 with hydrochloric acid to convert soap into free fatty acids that precipitated from the liquid, and (iii) precipitated free fatty acids were separated from the crude glycerol solution after centrifugation at 5000 rpm.

Analysis

The fungal mycelium in each flask was filtered through filter paper, rinsed twice with distilled water, and freeze-dried to constant weight. The freeze-dried fungal biomass was used for measuring the cell dry weight and then used for fatty acid analysis. Cell dry weight was determined by transferring a 5 mL cell suspension into a pre-weighed centrifuge tube that was then centrifuged at 3444 g for 5 min. The cell pellet was washed twice with distilled water, and then dried at 80° C. to constant weight. Glucose concentration was determined by the 3,5-dinitrosalicylic method (Miller, G. 1959. Analytical Chemistry, 31, 426-429). Glycerol concentration was determined by a Shimadzu Prominence HPLC System (Shimadzu Scientific Instruments, Inc. Columbia, Md.) with a pulsed refractive index detector. An Aminex HPX-87H (Bio-Rad, Sunnyvale, Calif.) column was used with 0.1% (v/v) $H_2SO_4$ solution as mobile phase. The flow rate was controlled at 0.6 mL/min, and the column temperature was 65° C.

Fatty acid methyl esters (FAME) were prepared by direct-methylation with 5% methanolic HCl (Christie, W. W. 2003. Lipid Analysis: Isolation, Separation, Identification and Structural Analysis of Lipids. Bridgwater, U.K.: The Oily Press; Schreiner, M. 2006. International Journal of Food Properties, 9, 573-581; Ulberth, F. & Henninger, M. 1992. Journal of the American Oil Chemists Society, 69, 174-177) and determined by a Shimadzu 2010 gas chromatograph (Shimadzu Scientific Instruments, Columbia, Md.) equipped with a flame-ionization detector and a SGE SolGel-Wax™ capillary column (30 m×0.25 mm×0.25 um). The injector was kept at 250° C., with an injection volume of 1 μl by split injection mode (10:1 ratio). The column temperature profile was as follows: 80° C. for 0.5 min; raised to 175° C. at 30° C./min; raised to 260° C. at 5° C./min; maintained for 6 min; raised to 280° C. at 30° C./min; maintained for 1 min. The detector temperature was kept at 300° C. The fatty acids of the algae sample were identified by comparing the retention times with those of fatty acid standards (Nu-Chek Prep Inc., MN), and quantified by comparing their peak areas with that of the internal standard (C17:0) (Chi, Z., Pyle, D., Wen, Z., Frear, C. & Chen, S. 2007. Process Biochemistry, 42, 1537-1545).

Feasibility of Producing EPA from Crude Glycerol

Figure 1B:
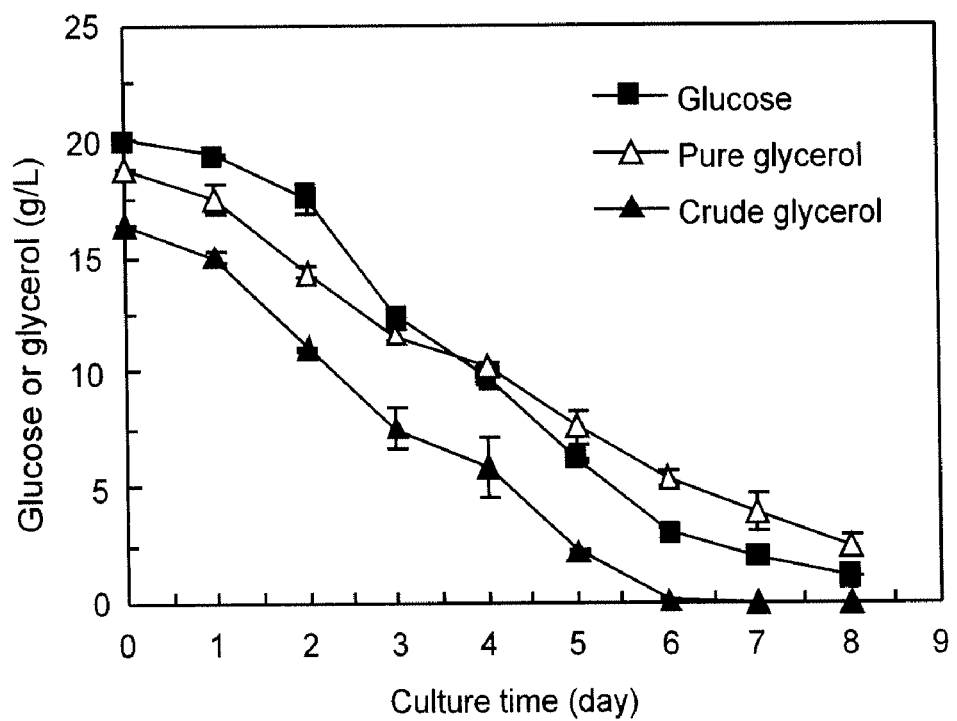

Growth performance and EPA production of *P. irregulare* were evaluated by growing the fungus in media containing glucose, pure glycerol, or crude glycerol as a carbon source. As shown in FIG. 1A, the glucose-containing medium resulted in the highest cell growth; crude glycerol and pure glycerol also supported cell growth, although the biomass was lower than in glucose culture. In terms of substrate consumption, the initial concentrations of the three carbon sources were around 20 g/L, the "real" glycerol concentration in crude glycerol culture was lower than 20 g/L due to the impurities contained in the crude glycerol fluid. As shown in FIG. 1B, the fungi fed with crude glycerol consumed all the substrate, while the other two cultures left residual substrate when the cells reached the stationary phase. This result indicates glycerol is the limiting substrate; therefore, increasing the crude glycerol level may further enhance cell growth. The fatty acid profiles of the fungal biomass derived from different carbon sources were also compared. As shown in Table 1, the major fatty acids were C16:0 and C18s. EPA accounted for 6-10% of total fatty acids in the biomass. The EPA level in terms of content, yield, and productivity from crude glycerol and pure glycerol cultures were similar, with both being lower than those from glucose medium. In the following sections, we optimized the culture conditions for the crude glycerol-culture to further increased the EPA production level from crude glycerol.

TABLE 1

Fatty acid composition, total fatty acid (TFA) content, and EPA production parameters of *P. irregulare* with glucose, pure glycerol, and crude glycerol as substrates[a]

| Fatty acid | Unit | Crude glycerol | Pure glycerol | Glucose |
|---|---|---|---|---|
| 14:0 | % TFA | 7.44 ± 0.056 | 5.56 ± 1.95 | 8.23 ± 0.36 |
| 16:0 | % TFA | 25.07 ± 0.51 | 25.51 ± 0.81 | 26.1 ± 0.79 |
| 16:1 | % TFA | 15.12 ± 0.73 | 10.05 ± 2.21 | 7.10 ± 0.64 |
| 18:0 | % TFA | 1.41 ± 0.04 | 18.66 ± 14.27 | 2.68 ± 0.10 |
| 18:1 | % TFA | 20.69 ± 0.33 | 23.92 ± 12.1 | 17.72 ± 0.95 |
| 18:2 | % TFA | 16.81 ± 0.35 | 6.43 ± 8.39 | 18.73 ± 0.75 |
| 20:4 (ARA) | % TFA | 6.21 ± 0.04 | 3.35 ± 2.01 | 8.7 ± 0.55 |
| 20:5 (EPA) | % TFA | 7.26 ± 0.5 | 6.53 ± 1.01 | 9.90 ± 0.42 |
| TFA content | mg/g DW | 260.63 ± 23.3 | 212.62 ± 21.17 | 198.19 ± 7.81 |
| EPA content | mg/g DW | 18.92 ± 0.11 | 14.08 ± 0.84 | 19.71 ± 1.12 |
| EPA yield | mg/L | 47.86 ± 2.02 | 41.81 ± 1.56 | 90.09 ± 5.65 |
| EPA productivity | mg/L-day | 7.99 ± 0.34 | 6.97 ± 0.26 | 15.01 ± 0.92 |

[a]Data are expressed as mean ± SD of three replicates.
DW: cell dry weight.

Optimization of Fungal Culture Conditions for Producing EPA from Crude Glycerol

The growth conditions, including medium composition and temperature, for the fungal culture were further optimized to enhance the EPA production. Experiments have shown that no fungal growth was observed in soap-containing medium, thus, soap was removed from the crude glycerol medium. Also, the methanol residue within the crude glycerol was completely evaporated during autoclaving.

Unlike the algae *S. limacinum* that has a complex nutrients requirement, *P. irregulare* requires a relatively simple medium composition, with glycerol and yeast extract being the only two components. The cell growth and EPA production in medium containing different combinations of these two components were investigated. As shown in Table 2, at low yeast extract levels (e.g., 5 and 10 g/L), the cell dry weight increased with increasing glycerol concentration. When yeast extract was at high levels (15 and 20 g/L), the cell dry weight remained stable, independent of the glycerol concentration. In terms of EPA production, the EPA content was significantly influenced by the yeast extract concentration; low levels (e.g., 5 g/L) resulted in a higher EPA content. This result agreed with algal cultures such as *Botryococcus braunii, Dunaliella bardawil, and Dunaliella salina* in which a higher percentage of EPA was obtained under low nitrogen levels (Benamotz, A., Tornabene, T. G. & Thomas, W. H. 1985. Journal of Phycology, 21, 72-81). Combining cell dry weight and EPA content, the highest EPA yield (ca. 80-90 mg/L) and EPA productivity (11-12 mg/L-day) were obtained in the range of 30-40 g/L crude glycerol and 5-10 g/L yeast extract (Table 2); therefore, we selected 30 g/L crude glycerol and 10 g/L yeast extract in the following temperature study.

Figure 2:
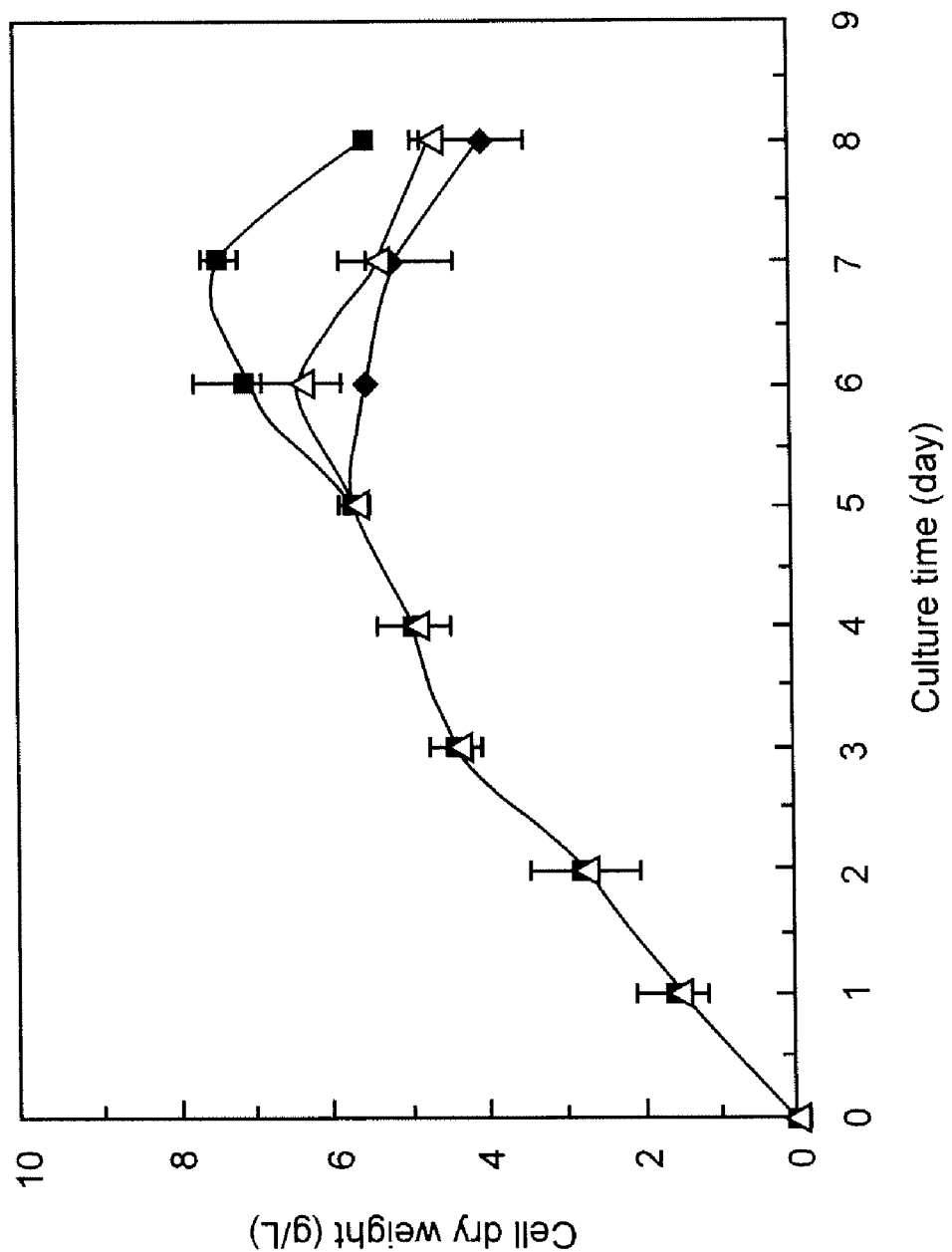
FIG. 2. Cell growth of *P. irregulare* at different temperature levels. (The fungi were grown at 25° C. for 5 days and then switched to 15° C., 20° C., or 25° C.). Symbols for different temperature levels: -△-: 25° C.; -●-15° C.; -■-20° C.

Temperature is another important factor influencing cell growth and lipid composition of many EPA-producing microorganisms. In general, higher temperatures lead to rapid cell growth while lower temperatures result in the accumulation of omega-3 fatty acids. Low temperature stress usually leads to a higher level of intracellular $O_2$, which favors the synthesis of long chain omega-3 fatty acids (Feng, C. & Johns, M. R. 1991. Journal of Applied Phycology, 3, 203-209.; Singh, A. & Ward, O. P. 1997. Advances in Applied Microbiology, 45, 271-312). A temperature shift strategy has been used to enhance the overall EPA production of *P. irregulare* grown on glucose (Stinson, E. E., Kwoczak, R. & Kurantz, M. J. 1991. Journal of Industrial Microbiology, 8, 171-178). Here, we used this "temperature shift" strategy to investigate the effect of temperature on the growth and EPA production of *P. irregulare* when crude glycerol was used as a carbon source. The fungal cells were grown at 25° C. for the first 5 days and then switched to 20° C. or 15° C. or kept at 25° C. As shown in FIG. 2, when the temperature was switched to 20° C., the fungal cells continued to grow for the next two days and reached the highest level of 7.33 g/L. This fungal biomass was even higher than that obtained at 25° C. The cell dry weight began to drop when the temperature was switched to 15° C., indicating that cell growth was inhibited at this temperature level. As for the EPA production (Table 3), 20° C. also resulted in a much higher EPA content than the other temperature levels. The EPA content at 15° C. was just slightly higher than the EPA content at 25° C. The EPA yield and productivity at different temperature levels were similar to the fungal growth and EPA content, i.e., 20° C. resulted in the highest EPA yield and production. Overall, the above results clearly show that using the temperature switching strategy, 20° C. was the ideal temperature at the later stage of fungal culture when using crude glycerol as a carbon source, achieving a highest EPA yield and productivity of 182 mg/L and 26 mg/L-day.

TABLE 2

Effect of crude glycerol and yeast extract concentrations on growth and EPA production of *P. irregulare*[a]

| Crude glycerol (g/L) | Yeast extract (g/L) | Biomass (g/L) | EPA content (mg/g DW) | EPA yield (mg/L) | EPA productivity (mg/L-day) |
|---|---|---|---|---|---|
| 10 | 5 | 2.31 ± 0.01 | 18.86 ± 0.89 | 43.35 ± 2.14 | 7.22 ± 0.35 |
| 20 | 5 | 2.80 ± 0.28 | 18.66 ± 1.21 | 52.98 ± 3.89 | 7.56 ± 0.95 |
| 30 | 5 | 4.62 ± 0.22 | 18.16 ± 0.76 | 83.84 ± 6.11 | 10.49 ± 0.77 |
| 40 | 5 | 5.78 ± 0.43 | 16.39 ± 1.19 | 88.32 ± 6.57 | 11.04 ± 0.82 |
| 20 | 10 | 4.22 ± 0.45 | 13.91 ± 1.41 | 58.01 ± 6.78 | 10.75 ± 1.13 |
| 30 | 10 | 6.27 ± 0.51 | 12.67 ± 1.47 | 86.20 ± 8.85 | 12.31 ± 1.26 |
| 40 | 10 | 6.48 ± 0.46 | 13.50 ± 1.24 | 87.54 ± 8.08 | 12.50 ± 1.15 |
| 50 | 10 | 5.34 ± 0.28 | 13.17 ± 1.89 | 70.44 ± 9.52 | 10.06 ± 1.36 |
| 20 | 15 | 4.96 ± 0.05 | 12.50 ± 0.74 | 62.06 ± 3.07 | 8.87 ± 0.44 |
| 30 | 15 | 4.46 ± 0.24 | 11.02 ± 0.66 | 49.19 ± 1.50 | 7.02 ± 0.21 |
| 40 | 15 | 5.04 ± 0.88 | 12.13 ± 0.22 | 61.15 ± 8.83 | 8.74 ± 1.21 |
| 50 | 15 | 4.83 ± 0.30 | 10.77 ± 0.69 | 47.18 ± 4.02 | 6.74 ± 0.57 |
| 20 | 20 | 6.04 ± 0.14 | 10.20 ± 1.09 | 69.85 ± 5.77 | 11.41 ± 0.82 |
| 30 | 20 | 6.63 ± 0.21 | 9.54 ± 0.02 | 62.38 ± 6.56 | 8.91 ± 0.93 |
| 40 | 20 | 6.65 ± 0.79 | 9.02 ± 0.43 | 60.02 ± 6.05 | 8.57 ± 0.98 |

[a]The "real" glycerol content was 85% of crude glycerol concentration.
DW: cell dry weight

TABLE 3

Effects of temperature strategy on EPA production of *P. irregulare*.

| | Temperature | | |
|---|---|---|---|
| | 25° C. | 20° C. | 15° C. |
| EPA content (mg/g DW) | 14.24 ± 0.01 | 24.93 ± 2.17 | 15.63 ± 1.81 |
| EPA yield (mg/L) | 89.36 ± 7.25 | 182.50 ± 10.06 | 84.65 ± 8.27 |
| EPA productivity (mg/L-day) | 14.89 ± 1.21 | 26.07 ± 1.44 | 14.11 ± 1.38 |

(DW: cell dry weight)

The above results demonstrate that crude glycerol can be used as a carbon source for EPA production by the fungi *P. irregulare*. The production level is comparable to that from glucose culture. The EPA-fungal biomass, together with the DHA-algal biomass, provides an alternative use for biodiesel-derived crude glycerol by producing a balanced omega-3 source for fortified food or animal feed.

Example 2

Use of Biodiesel-Derived Crude Glycerol for Producing Eicosapentaenoic Acid (EPA) by the Fungus *Pythium irregulare*

When *P. irregulare* was grown in medium containing 30 g/L crude glycerol and 10 g/L yeast extract, EPA yield and productivity reached 90 mg/L and 14.9 mg/L per day, respectively. Adding pure vegetable oils (flaxseed oil and soybean oil) to the culture greatly enhanced the biomass and the EPA production. This enhancement was due to the oil absorption by the fungal cells and elongation of shorter chain fatty acids (e.g., linoleic acid and alpha-linolenic acid) into longer chain fatty acid (e.g., EPA). The major impurities contained in crude glycerol, soap and methanol, were inhibitory to fungal growth. Soap can be precipitated from the liquid medium through pH adjustment, whereas methanol can be evaporated from the medium during autoclaving. The glycerol-derived fungal biomass contained about 15% lipid, 36% protein, and 40% carbohydrate, with 9% ash. In addition to EPA, the fungal biomass was also rich in the essential amino acids lysine, arginine, and leucine, relative to many common feedstuffs. Elemental analysis by inductively coupled plasma showed that aluminum, calcium, copper, iron, magnesium, manganese, phosphorus, potassium, silicon, sodium, sulfur, and zinc were present in the biomass, whereas no heavy metals (such as mercury and lead) were detected. The results show that it is feasible to use crude glycerol for producing fungal biomass that can serve as EPA-fortified food or feed.

Materials and Methods

Crude Glycerol Source. Crude glycerol used in this study was a dark brown stream obtained from Virginia Biodiesel Refinery (West Point, Va.). The refinery used alkali (KOH)-catalyzed transesterification of soybean oil with methanol for producing biodiesel. The crude glycerol resulting from this process (pH~12) contains approximately 20% (w/w) soap residues. When this glycerol is pH-adjusted to 6.0-6.5, which is more suitable for fungus growth, soaps are converted into free fatty acids.

Fungal Species and Culture Conditions. *P. irregulare* (ATCC 10951) was Used in this experiment. The organism used to be classified as a fungus; recent taxonomic definitions of *Pythium* have been changed to the Kingdom Chromista (algae). In this Example, the term fungus is used to define *Pythium* in order to keep our terminology consistent with other papers. The fungus was grown on agar plates that were prepared by dissolving 20 g/L glucose and 10 g/L yeast extract (Acros Organics, Fail Lawn, N.J.) in water with the addition of 1.5% (w/w) of agar (Fluka, Sigma-Aldrich, Mo.). The pH of this agar medium was 5.8-5.9. After 5 days of incubation at a temperature of 25° C., the agar plates were washed with distilled water containing glass beads to dislodge the spores. This spore suspension was used as inoculum for further trials. The inoculum size was 10% (v/v) of the total culture medium.

In the study of EPA production from crude glycerol, the fungal cells were grown in medium containing 30 g/L crude glycerol and 10 g/L yeast extract. The pH was adjusted to 6.0-6.5 before the medium was autoclaved at 121° C. for 15 min. The cells were grown in 250 mL Erlenmeyer flasks, each containing 50 mL of medium, and incubated at 25° C. in an orbital shaker set to 170 rpm. For each experimental condition, three replicates were used, and the standard deviation was calculated.

Depending on the experimental conditions, soaps were either removed from or remained in the culture medium. The preparation of soap-free medium was the same as described previously (Pyle, D. J.; Garcia, R. A.; Wen, Z. Y. J. Agric. Food Chem. 2008, 56, 3933-3939). In brief, the crude glycerol was mixed with distilled water to reduce the fluid viscosity and then pH-adjusted to 3 with hydrochloric acid; the free fatty acids that precipitated from the liquid were separated by centrifugation at 5000 rpm. Then, yeast extract was added to the glycerol solution at the desired level and the medium pH was adjusted to 6.0-6.5. To prepare soap-containing medium, the soap that was originally precipitated from crude glycerol was spiked back into the culture medium at the desired levels.

Analysis. Cell Dry Weight. The fungal biomass from each flask was harvested, vacuum-filtered through Whatman No. 1 filter paper, and washed with 25 mL of distilled water. The biomass was then transferred to a preweighed tube and freeze-dried (model 12SL freeze drier, The Virtis Co., Gardiner, N.Y.). After the dry weight had been measured, the freeze-dried biomass was used for proximate, fatty acid, amino acid, and elemental analyses. Glycerol Concentration. Glycerol concentrations were determined by a Shimadzu Prominence HPLC System (Shimadzu Scientific Instruments, Inc., Columbia, Md.) with a refractive index detector. An Aminex HPX-87H (Bio-Rad, Sunnyvale, Calif.) column was used with 0.1% (v/v) $H_2SO_4$ solution as mobile phase. The flow rate was controlled at 0.6 mL/min, and the column temperature was 65° C.

Proximate Analysis. The lipids from the freeze-dried biomass were extracted and quantified according to the Bligh and Dyer method (25). The protein content was estimated by summation of each amino acid. The nonprotein nitrogen (NPN) content was determined by subtracting protein nitrogen (PN) from the total nitrogen (TN) of the biomass. Here, TN was determined according to the Kjehldahl method; PN was estimated by dividing the protein content by 6.25. The ash content was determined by heating the sample at 550° C. overnight and weighing the remaining matter. The carbohydrate was then calculated by subtraction.

Fatty Acid, Amino Acid, and Elemental Analysis. Fungal biomass, vegetable oils, and the soap were analyzed for their fatty acid compositions. The protocols for fatty acid methyl esters (FAME) preparation and the gas chromatography analyses were the same as in Example 1. To analyze amino acid composition, the fungal biomass was first defatted with hexane to reduce interference. The defatted biomass was then analyzed chromatographically for its amino acid composition using the methods described in Example 1. The elemental composition of the fungal biomass was determined by an inductively coupled plasma semiquantitative scan of 69 elements according to EPA method SW-846 6010B (SuperScan 69 performed by Prochem Analytical Inc., Elliston, Va.). EPA method SW-846 7471A was further used to detect any trace amount of mercury possibly contained in the biomass; the detection limit for this measurement was 0.025 ppm (25 ppb).

Results

Growth Characteristics and EPA Production.

Figure 3A:
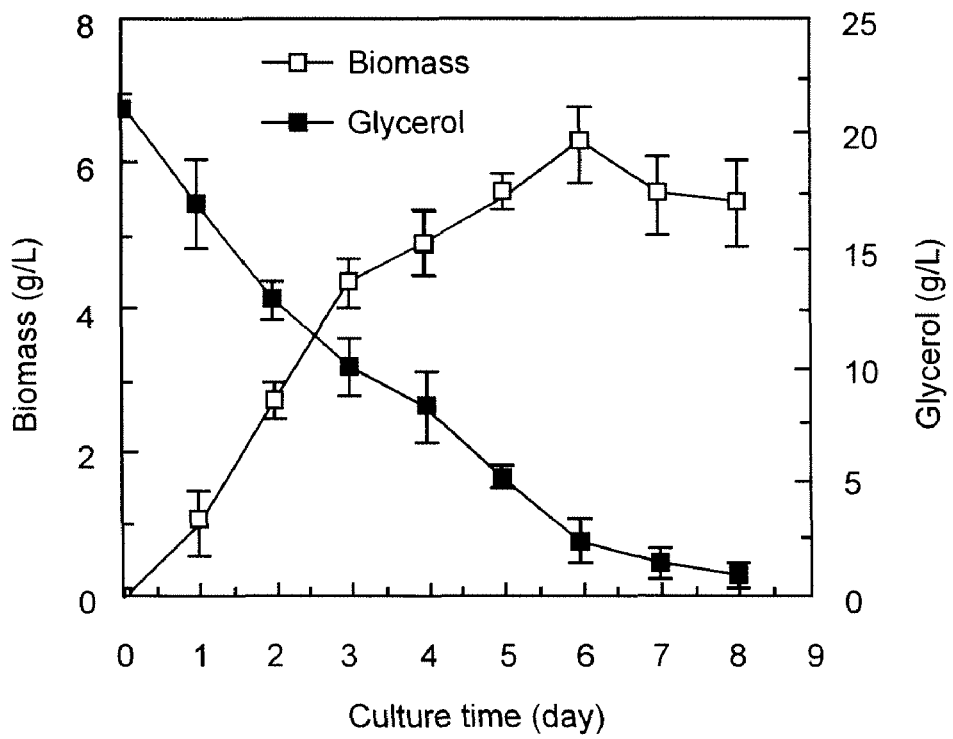
FIGS. 3A and B. Time course of biomass, residual glycerol concentration (A); EPA content and total fatty acids (TFA) content (B) of *P. irregulare* grown in medium containing 30 g/L crude glycerol and 10 g/L yeast extract. Data are means of three replicates, and error bars show standard deviations.
Figure 3B:
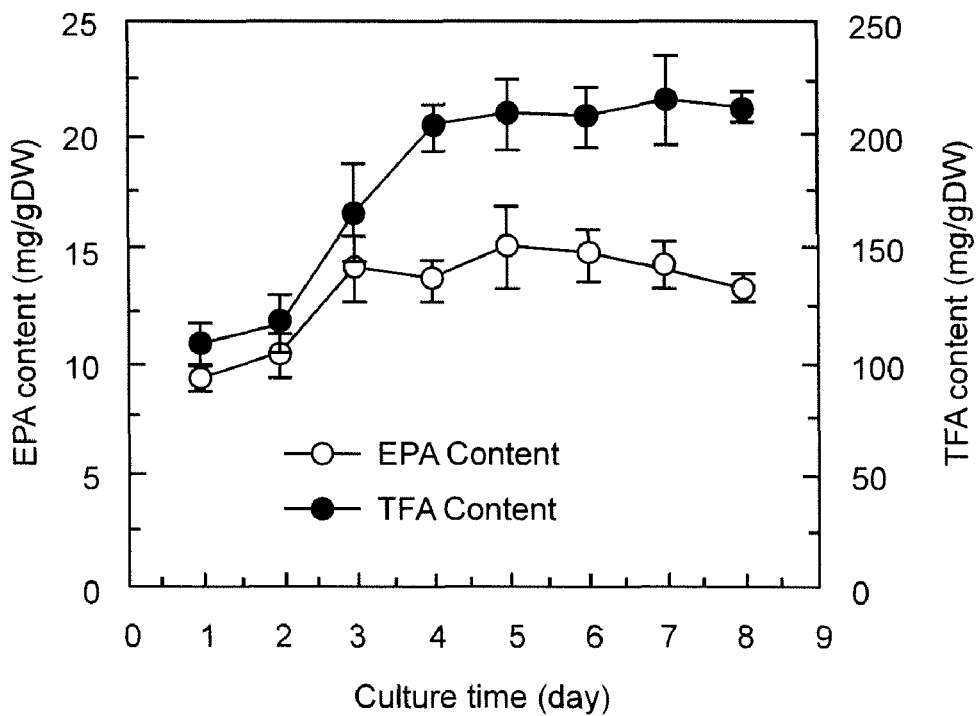

*P. irregulare* was grown in medium containing 30 g/L crude glycerol and 10 g/L yeast extract. When the impurities in crude glycerol were accounted for, the "real" glycerol concentration in the medium was 22 g/L. As shown in FIG. 3A, maximum biomass value of 6.31 g/L was reached at day 6 when glycerol was almost completely consumed. FIG. 3B shows that both the total fatty acids (TFA) and EPA contents increased through the first 3-4 days and leveled off at a later stage of culture. The growth kinetics and EPA production parameters are summarized in Table 4. The specific growth rate (0.512 day-1) and the growth yield coefficient based on glycerol (0.33 g/g) were comparable to those of other omega-3 fatty acid-producing species grown in crude glycerol.

Fungal Culture with Added Vegetable Oils

Figure 4:
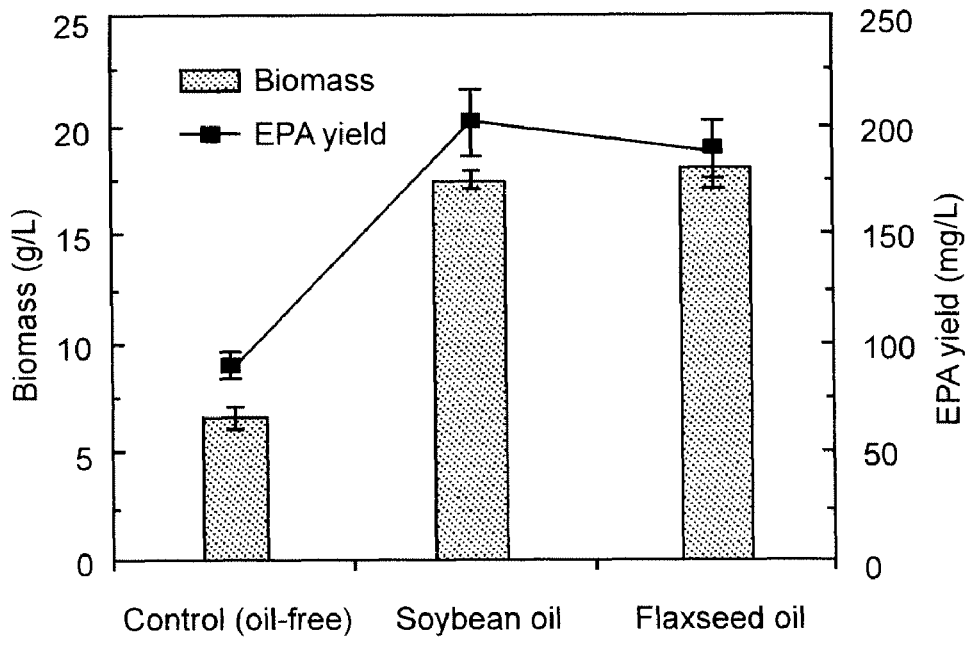
FIG. 4. Biomass and EPA yield of *P. irregulare* grown in crude glycerol medium with different vegetable oils added at 1%. Data are means of three replicates, and error bars show standard deviations.

Pure vegetable oils (soybean oil and flaxseed oil) were added to the culture of *P. irregulare* to investigate if this addition would enhance the fungal growth and EPA production. We ensured the shaking was strong enough to disperse the oil into small droplets so the fungal biomass could access it. As shown in FIG. 4, addition of vegetable oils appreciably increased the biomass and EPA yield (units) mg/L) compared with the control (oil-free) culture. Soybean oil and flaxseed oil resulted in similar enhancements. However, due to the different fatty acid profiles contained in these two types of vegetable oils, the fatty acid compositions of the resulting biomasses were quite different. As shown in Table 5, flaxseed oil had an appreciable amount of alpha-linolenic acid (C18:3), whereas soybean oil was rich in linoleic acid (C18:2). The fungal biomasses derived from these two types of oil culture had fatty acid distributions similar to that of the feedstock oil. Table 2 also shows that the TFA content of the oil-added biomass was much higher than that of the control. However, both EPA percentage (% TFA) and content (mg/g of DW) of the oil-derived biomass were reduced compared with those of the control (Table 5). Therefore, the increase of EPA yield was due to the increase in biomass (FIG. 4).

TABLE 5

Fatty Acid Compositions of the Vegetable Oils and the Fungal Biomass Derived from Oil Addition Cultures[a]

| fatty acid | unit | control (oil free) fungal biomass | flaxseed oil addition | | soybean oil addition | |
|---|---|---|---|---|---|---|
| | | | flaxseed oil | fungal biomass | soybean oil | fungal biomass |
| C14:0 | % TFA[b] | 7.76 ± 0.74 | nd[c] | 0.36 ± 0.01 | nd | 0.17 ± 0.01 |
| C16:0 | % TFA | 25.25 ± 3.24 | 5.51 ± 0.01 | 11.26 ± 0.01 | 10.48 ± 0.44 | 10.75 ± 0.08 |
| C16:1 | % TFA | 13.58 ± 0.15 | nd | 1.44 ± 0.09 | nd | 1.52 ± 0.01 |
| C18:0 | % TFA | 3.19 ± 0.02 | 2.87 ± 0.02 | 4.03 (0.09 | 4.36 (0.17 | 4.67 ± 0.02 |
| C18:1 | % TFA | 16.74 ± 0.02 | 16.45 ± 0.03 | 21.55 ± 0.64 | 24.83 ± 0.99 | 26.19 ± 0.08 |
| C18:2 (n-6) | % TFA | 18.37 ± 2.32 | 21.01 ± 0.02 | 14.28 ± 0.01 | 56.09 ± 2.48 | 54.05 ± 0.28 |
| C18:3 (n-3) | % TFA | nd | 54.15 ± 0.04 | 49.09 ± 0.06 | 6.77 ± 0.33 | nd |
| C20:4 (n-6) | % TFA | 6.79 ± 0.77 | nd | 0.75 ± 0.07 | nd | 0.89 ± 0.01 |
| C20:5 (n-3) | % TFA | 12.55 ± 1.05 | nd | 2.21 ± 0.16 | nd | 2.64 ± 0.23 |
| EPA content | mg/g of DW | 14.93 ± 0.68 | na | 10.67 ± 0.72 | na | 11.42 ± 0.87 |
| TFA content | mg/g of DW | 119.01 ± 9.94 | na | 496.42 ± 14.59 | na | 427.34 ± 18.89 |

[a]Data are means of three replicates (standard deviations.
[b]TFA, total fatty acids.
[c]nd, not detected;
na, not applicable.

TABLE 4

Cell Growth and EPA Production Parameters of *P. irregulare*[a]

| parameter | unit | value |
|---|---|---|
| max cell dry wt, $X_{max}$ | g/L | 6.31 0.43 |
| specific growth rate | day$^{-1}$ | 0.512 ± 0.023 |
| biomass productivity | g/L · day | 1.05 ± 0.09 |
| growth yield, $Y_{X/S}$ | g/g | 0.33 ± 0.02 |
| EPA content | mg/g of DW | 14.71 ± 1.01 |
| EPA yield | mg/L | 89.76 ± 7.25 |
| EPA productivity | mg/L · day | 14.96 ± 1.21 |

[a]Data are means of three replicates ± standard deviations.

Effects of Soap

The effects of soap on fungal growth and EPA production were first studied by inoculating fungal spores to the soap-containing medium. However, no cell growth was observed in the soap-containing medium, which may be due to the soap enveloping the fungal spores and cutting off the nutrient and oxygen supplies. To alleviate this inhibition, we grew the spores in soap-free medium for a period of time (3 days) until a clump of fungal mycelium was observed; this mycelium was then inoculated into medium with added soap. With the crude glycerol concentration (30 g/L) and soap content (~20%) commonly used, the soap concentration in the medium would be 6 g/L if not removed. Therefore, we adjusted the soap addition level at 1, 2, 4, and 6 g/L.

Figure 5:
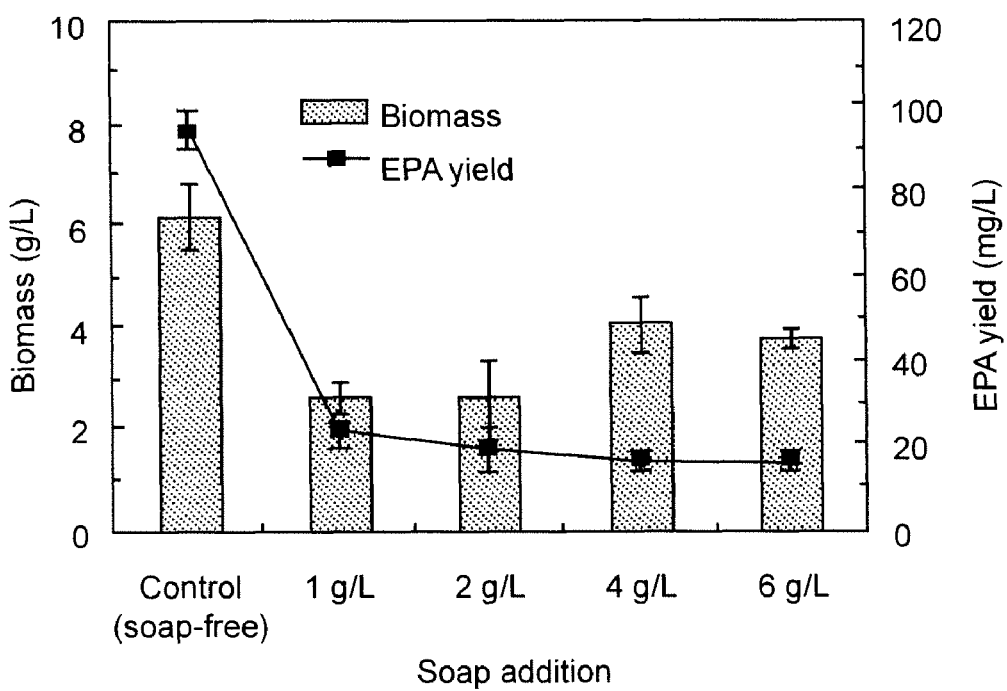
FIG. 5. Biomass and EPA yield of *P. irregulare* grown in crude glycerol medium with different levels of soap residues added. Data are means of three replicates, and error bars show standard deviations.

As shown in FIG. 5, the fungal biomass in medium with added soap was lower than that in soap-free medium. The EPA production was also inhibited with the addition of soap, as evidenced by the sharp decrease of EPA yield even with a soap addition as low as 1 g/L (FIG. 5). Table 6 shows the fatty acid composition of the soap and the fungal biomass growing in media with different levels of soap. The soap mainly contained C18:1 and C18:2 fatty acids, which accounted for 80% of the TFA. When this soap was added to the medium, independent of the soap amount, the resulting biomass had about 18-19% of C16:0, 31-32% of C18:1, and 35-38% of C18:2. The EPA (C20:5) percentage in TFA of the control (soap-free) biomass was about 12%, whereas this percentage was reduced (0.85-2.31%) when the fungus was grown in soap-containing medium (Table 6). It was also found that the soap addition appreciably increased the TFA content of the biomass (Table 6). However, this increase could not compensate for the loss of EPA percentage in TFA; as a result, EPA content per unit of biomass was decreased with the addition of soap to the crude glycerol medium.

these two impurities can be removed from the culture medium in relatively easy ways. Soap can be precipitated from the solution by pH adjustment and then removed through phase separation; methanol can be evaporated during autoclaving of the medium. In this study, the fungal biomass obtained from this soap- and methanol-free medium was characterized in terms of its nutritional values and elemental composition.

Table 7 shows the proximate analysis of the biomass. Lipid, protein, and carbohydrate were the three major components of the biomass. The nonprotein nitrogen content of the biomass was 2.31% (Table 7). The fatty acid profile of the fungal biomass is presented in Tables 5 and 6 (the "control"); the major fatty acids were C16:0 and C18 with EPA accounting for 12% of TFA. In addition to EPA, the fungus also contained small amounts of C14:0 and C20:4 (arachidonic acid, AA). The amino acid composition shows that the fungal biomass was rich in asparagine plus aspartic acid and glutamine plus glutamic acid (>10% of total protein each) followed by leucine and lysine (Table 8). Table 9 shows the results of ICP elemental analysis of the fungal biomass. The

TABLE 6

Fatty Acid Compositions of the Soap and Fungal Biomass Growing in Crude Glycerol Medium with Added Soap[a]

| fatty acid | unit | soap | control (soap-free) | fungal biomass grown at different soap levels | | | |
|---|---|---|---|---|---|---|---|
| | | | | 1 g/L | 2 g/L | 4 g/L | 6 g/L |
| C14:0 | % TFA[b] | nd[c] | 7.43 ± 0.34 | 1.46 ± 0.26 | 1.03 ± 0.00 | 0.81 ± 0.03 | 0.84 ± 0.07 |
| C16:0 | % TFA | 10.89 ± 0.14 | 21.61 ± 0.40 | 19.06 ± 0.15 | 18.92 ± 0.80 | 18.98 ± 0.46 | 19.3 ± 0.57 |
| C16:1 | % TFA | nd | 12.46 ± 1.14 | 4.59 ± 0.19 | 4.07 ± 0.22 | 3.76 ± 0.02 | 3.88 ± 0.19 |
| C18:0 | % TFA | 5.42 ± 0.23 | 1.51 ± 0.06 | 4.37 ± 0.19 | 4.59 ± 0.01 | 4.82 ± 0.03 | 4.72 ± 0.03 |
| C18:1 | % TFA | 24.38 ± 1.47 | 16.57 ± 0.42 | 31.51 ± 0.16 | 31.93 ± 1.08 | 32.23 ± 0.22 | 32.48 ± 0.24 |
| C18:2 (n-6) | % TFA | 56.77 ± 2.88 | 18.17 ± 0.4 | 35.42 ± 0.72 | 37.07 ± 0.42 | 38.05 ± 0.39 | 37.31 ± 1.03 |
| C18:3 (n-3) | % TFA | 4.83 ± 0.21 | nd | nd | nd | nd | nd |
| C20:4 (n-6) | % TFA | nd | 7.07 ± 0.78 | 1.29 ± 0.21 | 0.92 ± 0.01 | 0.63 ± 0.04 | 0.57 ± 0.02 |
| C20:5 (n-3) | % TFA | nd | 11.89 ± 0.56 | 2.31 ± 0.17 | 1.48 ± 0.09 | 0.85 ± 0.05 | 0.89 ± 0.12 |
| EPA content | mg/g of DW | na | 15.31 ± 0.71 | 8.63 ± 0.41 | 7.12 ± 0.62 | 3.97 ± 0.26 | 4.14 ± 0.55 |
| TFA content | mg/g of DW | na | 128.79 ± 11.90 | 373.87 ± 17.56 | 481.49 ± 41.92 | 525.89 ± 22.39 | 465.94 ± 32.35 |

[a]Data are means of three replicates (standard deviations.
[b]TFA, total fatty acids.
[c]nd, not detected;
na, not applicable.

Effects of Methanol

The crude glycerol used in this work contained ~12% (w/w) methanol. When 30 g/L crude glycerol concentration was used in this study, the methanol concentration was about 3.6 g/L. It was found that this amount of methanol was completely evaporated when the medium was autoclaved at 121° C. for 15 min. To study the "true" effects of methanol on fungal growth and EPA production, we prepared a medium containing 20 g/L pure glycerol spiked with 2, 4, and 8 g/L methanol. The medium was then passed through a 0.2 μm filter before fungal spores were inoculated. However, we did not observe any growth in the methanol-containing medium (data not shown). The result clearly indicated the negative effects of methanol on growth and EPA production of *P. irregulare*.

Fungal Biomass Composition

The above results indicate that soap and methanol, two major impurities in crude glycerol, were inhibitory to the growth and EPA production of *P. irregulare*. Fortunately, biomass had a high potassium content, probably due to the high amount of potassium contained in the original crude glycerol solution as the biodiesel producer used a potassium hydroxide based transesterification process. No heavy metals such as mercury or lead were detected by the ICP analysis. Even specialized testing, using EPA method SW-846 7471A with a reporting limit of 0.025 ppm, did not detect any mercury in the algal biomass.

TABLE 7

Proximate Analysis of Freeze-Dried Fungal Biomass Grown on Crude Glycerol[a]

| composition | mass % of dry biomass |
|---|---|
| lipid | 15.29 ± 0.59 |
| protein | 35.64 ± 1.41 |
| carbohydrate | 40.09 ± 0.74 |
| total nitrogen | 8.02 ± 0.04 |

TABLE 7-continued

Proximate Analysis of Freeze-Dried Fungal
Biomass Grown on Crude Glycerol[a]

| composition | mass % of dry biomass |
| --- | --- |
| nonprotein nitrogen | 2.31 ± 0.07 |
| ash | 8.97 ± 0.63 |

[a]Data are means of three replicates ± standard deviations.

TABLE 8

Amino Acid Composition of Fungal
Biomass Grown on Crude Glycerol[a]

| amino acid | mass % of protein | mg/g of dry biomass |
| --- | --- | --- |
| Asx[b] | 10.18 ± 0.07 | 36.28 ± 1.27 |
| Ser | 4.34 ± 0.03 | 15.47 ± 0.56 |
| Glx[b] | 15.60 ± 0.16 | 55.62 ± 2.20 |
| Gly | 4.21 ± 0.01 | 15.03 ± 0.61 |
| His | 2.60 ± 0.01 | 9.29 ± 0.41 |
| NH$_3$[c] | 2.84 ± 0.02 | 10.12 ± 0.43 |
| Arg | 6.54 ± 0.07 | 23.33 ± 1.00 |
| Thr | 4.89 ± 0.01 | 17.43 ± 0.70 |
| Ala | 5.61 ± 0.01 | 20.01 ± 0.75 |
| Pro | 3.61 ± 0.04 | 12.89 ± 0.57 |
| Tyr | 4.11 ± 0.04 | 14.66 ± 0.65 |
| Val | 5.87 ± 0.09 | 20.94 ± 0.99 |
| Ile | 4.88 ± 0.08 | 17.41 ± 0.83 |
| Leu | 7.71 ± 0.10 | 27.48 ± 1.24 |
| Lys | 7.67 ± 0.08 | 27.36 ± 1.18 |
| Phe | 4.90 ± 0.07 | 17.48 ± 0.82 |
| Cys[d] | 1.93 ± 0.15 | 6.88 ± 0.48 |
| Met[d] | 2.44 ± 0.17 | 8.71 ± 0.64 |

[a]Data are means of three replicates ± standard deviations.
[b]Glx = Glu + Gln; Asx = Asp + Asn.
[c]NH$_3$ resulted from the deamination of asparagine and glutamine during the analysis process.
[d]Cys and Met were oxidized quatitatively and measured as cysteic acid and methionine sulfone, respectively.

TABLE 9

Elemental Composition of Fungal Biomass
As Detected by ICP Analysis[a]

| element | detection limit (ppm) | content (mg/kg) |
| --- | --- | --- |
| aluminum | 10 | 12.10 ± 1.68 |
| calcium | 50 | 528 ± 31 |
| copper | 5 | 12.55 ± 0.21 |
| iron | 10 | 56.75 ± 3.89 |
| magnesium | 50 | 310 ± 2 |
| manganese | 2 | 2.95 ± 0.64 |
| phosphorus | 50 | 7795 ± 134 |
| potassium | 100 | 19700 ± 1131 |
| silicon | 10 | 72.8 ± 5.5 |
| sodium | 50 | 1380 ± 127 |
| sulfur | 100 | 3875 ± 191 |
| zinc | 2 | 122 ± 8 |

[a]Data are means of three replicates ± standard deviations. A total of 69 elements as described in Table 1 of ref 18 were analyzed; the elements listed in this table were detected in the fungal biomass.

Discussion

*P. irregulare* has shown to be capable of using a variety of substrates for its growth and EPA production, such as soymeal waste, crude soybean oil, sucrose waste stream (Cheng, M. H.; Walker, T. H.; Hulbert, G. J.; Raman, D. R. Bioresour. Technol. 1999, 67, 101-110), or sweet whey permeate (Obrien, D. J.; Kurantz, M. J.; Kwoczak, R. Appl. Microbiol. Biotechnol. 1993, 40, 211-214.). Example 1 showed the feasibility of growing *P. irregulare* using biodiesel-derived crude glycerol. The EPA production level obtained from crude glycerol culture was comparable to those reported using glucose or other organic waste materials. It has shown that adding soybean oil to glucose-based culture of *P. irregulare* enhanced fungal growth and EPA accumulation (Cheng et al., 1999). We observed a similar phenomenon with the crude glycerol-based culture with added flaxseed oil or soybean oil (FIG. 4). The increase of biomass was due to the storage of excess oil in the fungal cells. As shown in Table 5, flaxseed oil contained an appreciable amount of alpha-linolenic acid (C18:3 n-3), whereas soybean oil was rich in linoleic acid (C18:2 n-6); when the two oils were added to the culture medium, their resultant biomass contained a high proportion of these two fatty acids. The TFA contents in oil-added biomass were also much higher than that of the control (oil-free). All of these results indicate the storage of excess oil in the fungal cells (Table 5).

The storage of linoleic acid (C18:2 n-6) and alpha-linolenic acid (C18:3 n-3) in the fungal cells can also serve as precursors for the synthesis of longer chained fatty acid such as EPA. In general, EPA can be synthesized through either the n-6 route (i.e., from linoleic acid to arachidonic acid and subsequently to EPA) or the n-3 route (i.e., from alpha-linolenic acid to EPA) (Shimizu, S.; Kawashima, H.; Akimoto, K.; Shinmen, Y.; Yamada, H. J. Am. Oil Chem. Soc. 1989, 66, 342-347; Wen, Z. Y.; Chen, F. Biotechnol. Adv. 2003, 21, 273-294). In the oil-free culture, *P. irregulare* synthesizes EPA mainly through the n-6 route rather than the n-3 route, because most fungi exhibit high activity of Δ12 desaturase that converts oleic acid into linoleic acid and Δ17 desaturase that converts arachidonic acid into EPA (Shimizu et al. 1989; Jareonkitmongkol, S.; Shimizu, S.; Yamada, H. J. Am. Oil Chem. Soc. 1993, 70, 119-123). The fatty acid distribution profile in the oil-free culture also confirms this hypothesis, as an appreciable amount of linoleic acid (C18:2) and arachidonic acid (C20:4) was in the fungal cells, whereas no alpha-linolenic acid (C18:3) existed (Table 5). When vegetable oils were added to the culture, flaxseed oil mainly provided alpha-linolenic acid (C18:3), whereas soybean oil mainly provided linoleic acid (C18:2), to the cells. The fungal cells can use these external precursors for *P. irregulare* to synthesize EPA. As a result, the overall EPA yield was increased in the oil addition cultures compared with oil-free culture (FIG. 4).

The proportions of EPA among total fatty acids (% TFA) and cellular content of EPA (mg/g of DW) were decreased in the oil-added cultures (Table 5). These decreases were caused by the "dilution" effect as more fat and biomass were accumulated in these cultures, and not all of this accumulated fat was converted into EPA.

The beneficial effects of adding vegetable oil on the culture of *P. irregulare* led us to explore the possible enhancement of fungal growth and EPA production when soap is included in the medium. Indeed, soap also contained high levels of C18 fatty acids (Table 6), which may serve as additional precursors for fungi to synthesize EPA (FIG. 5). However, both the fungal growth and the fatty acid composition from the soap addition culture (FIG. 5 and Table 6) suggest that instead of being beneficial, soap strongly inhibited the fungal growth and EPA production. In addition to soap, methanol also exhibited inhibitory effects on fungal growth.

Currently, there have been no reports on the chemical composition analyses of EPA-producing fungi, particularly *P. irregulare*. We therefore used the composition of DHA-producing *S. limacinum* derived from crude glycerol (Pyle, D. J.; Garcia, R. A.; Wen, Z. Y. J. Agric. Food Chem. 2008, 56, 3933-3939) as the "baseline" data to evaluate the quality of *P. irregulare* biomass. The chemical analysis of the biomass obtained from crude glycerol culture (soap- and methanol-free) shows that carbohydrate accounted for the biggest portion of the dried biomass followed by protein and the lipid (Table 7). Compared with *S. limacinum*, *P. irregulare* has fewer lipids but more proteins. The biomass is rich in the essential amino acids lysine, arginine, and leucine, which will increase its value as a feed ingredient. Overall, this amino acid distribution was similar to that of *S. limacinum*. Elemental analysis shows that the fungal biomass did not contain any toxic heavy metals such as mercury or lead (Table 9). However, modest amounts of aluminum and zinc need to be considered when the fungal biomass is developed as food or animal feed, as excessive levels of these metals can be damaging.

In summary, the above results indicate the great potential of producing EPA from biodiesel-derived crude glycerol by fungal fermentation.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of producing a fatty acid-rich biomass from crude waste glycerol, comprising the steps of
   providing crude glycerol in a culture medium, wherein said cude glycerol is substantially free of soaps and methanol; and
   culturing *Pythium* in said medium under conditions that permit said *Pythium* to use glycerol in said medium as a carbon source and producing a fatty acid-rich biomass.

2. The method of claim 1, wherein said *Pythium* is *Pythium irregulare*.

3. The method of claim 1, wherein said fatty acid-rich biomass comprises eicosapentaenoic acid (EPA).

4. The method of claim 1, wherein said step of providing includes a step of removing soaps and methanol from said crude glycerol.

5. The method of claim 1, wherein said crude glycerol culture medium further comprises one or more oils.

6. The method of claim 5, wherein said one or more oils is selected from flaxseed oil and soybean oil.

7. The method of claim 1, wherein crude glycerol is present in said crude glycerol culture medium at a concentration of 30 grams per liter.

8. The method of claim 1, wherein said crude glycerol culture medium further comprises 10 g/L of yeast extract.

9. A method of producing eicosapentaenoic acid (EPA) containing biomass from crude waste glycerol, comprising the steps of pretending said crude waste glycerol to obtain crude glycerol that is substantially free of soaps and methanol
   adding said pretreated crude glycerol to a culture medium; and
   culturing *Pythium* in said medium under conditions that permit said *Pythium* to use glycerol in said medium as a carbon source and producing EPA-containing biomass.

10. The method of claim 9, wherein said *Pythium* is *Pythium irregulare*.

11. The method of claim 9, wherein said crude glycerol culture medium further comprises one or more oils.

12. The method of claim 11, wherein said one or more oils is selected from flaxseed oil and soybean oil.

13. The method of claim 9, wherein crude glycerol is present in said crude glycerol culture medium at a concentration of 30 grams per liter.

14. The method of claim 9, wherein said crude glycerol culture medium further comprises 10 g/L of yeast extract.

* * * * *